(12) United States Patent
Wataya (10) Patent No.: US 9,661,997 B2
(45) Date of Patent: May 30, 2017

(54) ENDOSCOPE HAVING IMAGE SENSOR WITH SEGMENTATION REGION, FOR OUTPUTTING VIDEO, SHIFTED FROM CENTER OF PIXEL FORMATION REGION

(71) Applicant: OLYMPUS CORPORATION, Tokyo (JP)

(72) Inventor: Yuichi Wataya, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/041,154

(22) Filed: Feb. 11, 2016

(65) Prior Publication Data

US 2016/0157705 A1     Jun. 9, 2016

Related U.S. Application Data

(63) Continuation of application No. PCT/JP2014/076298, filed on Oct. 1, 2014.

(30) Foreign Application Priority Data

Oct. 17, 2013   (JP) ................. 2013-216566

(51) Int. Cl.
*A61B 1/05* (2006.01)
*A61B 1/00* (2006.01)
*A61B 1/018* (2006.01)

(52) U.S. Cl.
CPC ............ *A61B 1/05* (2013.01); *A61B 1/00009* (2013.01); *A61B 1/00087* (2013.01);
(Continued)

(58) Field of Classification Search
CPC ....... A61B 1/05; A61B 1/051; A61B 1/00009; A61B 1/00087; A61B 1/018; G02B 23/2484; H04N 5/2259
See application file for complete search history.

(56) References Cited

U.S. PATENT DOCUMENTS

| 4,773,396 A | 9/1988 | Okazaki |
| 5,235,965 A * | 8/1993 | Hiroya ................. A61B 1/0008 600/108 |

(Continued)

FOREIGN PATENT DOCUMENTS

| JP | S63-43639 A | 2/1988 |
| JP | S63-316013 A | 12/1988 |

(Continued)

OTHER PUBLICATIONS

International Search Report dated Jan. 20, 2015 issued in PCT/JP2014/076298.

(Continued)

*Primary Examiner* — John P Leubecker
(74) *Attorney, Agent, or Firm* — Scully, Scott, Murphy & Presser, P.C.

(57) ABSTRACT

An endoscope includes an image pickup unit and a treatment instrument channel. The image pickup unit and the treatment instrument channel are adjacent to each other. The image pickup unit includes an objective lens and an image pickup device. In a pixel formation region of the image pickup unit, a segmentation region is set as a region read out as a region for displaying a video. A center of the segmentation region is disposed to be shifted from a center of the pixel formation region toward the treatment instrument channel. An optical axis of the objective lens is parallel to a center axis of the treatment instrument channel. The center of the segmentation region is located on the optical axis.

9 Claims, 10 Drawing Sheets

(52) U.S. Cl.
CPC ...... *A61B 1/00096* (2013.01); *A61B 1/00163* (2013.01); *A61B 1/018* (2013.01); *A61B 1/051* (2013.01)

(56) References Cited

U.S. PATENT DOCUMENTS

| | | | | |
|---|---|---|---|---|
| 6,416,463 | B1* | 7/2002 | Tsuzuki | G02B 23/2423 600/104 |
| 2001/0016679 | A1* | 8/2001 | Futatsugi | A61B 1/05 600/133 |
| 2008/0088701 | A1* | 4/2008 | Unsai | A61B 1/00096 348/65 |
| 2008/0262297 | A1* | 10/2008 | Gilboa | A61B 1/00128 600/109 |
| 2013/0222562 | A1* | 8/2013 | Ono | A61B 1/00163 348/65 |
| 2014/0078276 | A1* | 3/2014 | Kaneko | G02B 23/243 348/65 |
| 2014/0232886 | A1* | 8/2014 | Takayama | H04N 5/23254 348/208.6 |

FOREIGN PATENT DOCUMENTS

| | | | |
|---|---|---|---|
| JP | H05-293079 A | | 11/1993 |
| JP | 09187419 A | * | 7/1997 |
| JP | H10-146312 A | | 6/1998 |

OTHER PUBLICATIONS

Japanese Office Action dated Jul. 14, 2015 issued in JP 2015-525668.

\* cited by examiner

ENDOSCOPE HAVING IMAGE SENSOR WITH SEGMENTATION REGION, FOR OUTPUTTING VIDEO, SHIFTED FROM CENTER OF PIXEL FORMATION REGION

CROSS REFERENCE TO RELATED APPLICATION

This application is a continuation application of PCT/JP2014/076298 filed on Oct. 1, 2014 and claims benefit of Japanese Application No. 2013-216566 filed in Japan on Oct. 17, 2013, the entire contents of which are incorporated herein by this reference.

BACKGROUND OF THE INVENTION

1. Field of the Invention

The present invention relates to an endoscope in which an image pickup device capable of reading out a pixel signal from any selected pixel among a plurality of pixels such as a MOS image sensor or a CMOS image sensor is used in an image pickup unit.

2. Description of the Related Art

In order to observe a place where observation is difficult such as an inside of a body of an organism or an inside of a structure, an endoscope including an image pickup unit for picking up an optical image in a distal end portion of an insertion section insertable from an outside into the inside of the organism or the structure is used in, for example, a medical field and an industrial field.

For example, as disclosed in Japanese Patent Application Laid-Open Publication No. H10-146312, an image pickup unit of an endoscope includes an objective lens that forms an object image and an image pickup device disposed on an image forming surface of the objective lens. A CCD (charge coupled device) is often used as the image pickup device of the image pickup unit of the endoscope.

In an endoscope including, in an insertion section, a treatment instrument channel for projecting treatment instruments such as a needle and a forceps from a distal end portion, outer diameters of the treatment instrument channel and the image pickup unit are relatively large among a plurality of components disposed at the distal end portion. Therefore, an outer diameter of the distal end portion of the insertion section of the endoscope including the treatment instrument channel is mainly set according to the outer diameters of the treatment instrument channel and the image pickup unit.

In general, in an image sensor capable of reading out a pixel signal from any selected pixel among a plurality of pixels such as a MOS image sensor or a CMOS (complementary metal oxide semiconductor) image sensor functioning as an image pickup device, compared with a CCD, a peripheral circuit formed around a pixel formation region is large.

SUMMARY OF THE INVENTION

An endoscope according to an aspect of the present invention includes: a distal end portion provided at a distal end of an insertion section; an image pickup unit provided at the distal end portion; and a treatment instrument channel provided at the distal end portion. At the distal end portion, the image pickup unit and the treatment instrument channel are adjacent to each other. The image pickup unit includes an objective lens and an image pickup device. The image pickup device is disposed such that a plane parallel to a device surface on which pixels are formed crosses a center axis of the treatment instrument channel, has a pixel formation region capable of receiving an optical image of the objective lens and converting the optical image into an electric signal, and is configured to be capable of reading out any pixel in the pixel formation region. In the pixel formation region, a segmentation region is set as a region read out as a region for displaying a video. A center of the segmentation region is disposed to be shifted from a center of the pixel formation region toward the treatment instrument channel. An optical axis of the objective lens is parallel to a center axis of the treatment instrument channel. The center of the segmentation region is located on the optical axis.

DETAILED DESCRIPTION OF THE PREFERRED EMBODIMENTS

Preferred embodiments of the present invention are explained below with reference to the drawings. Note that, in the respective figures used for the following explanation, in order to show respective components in recognizable sizes on the drawings, scales are varied for each of the components. The present invention is not limited to only numbers of the components, shapes of the components, ratios of sizes of the components, and relative positional relations among the respective components which are shown in the drawings.

First Embodiment

An example of an embodiment of the present invention is explained below. First, an example of a configuration of an endoscope 101 according to the present invention is explained with reference to FIG. 1. The endoscope 101 of the present embodiment has a configuration capable of being introduced into a subject such as a human body and capable of optically picking up a predetermined observation region in the subject. Note that the subject into which the endoscope 101 is introduced is not limited to the human body and may be other organisms or may be an artificial object such as a machine or a building.

Figure 1:
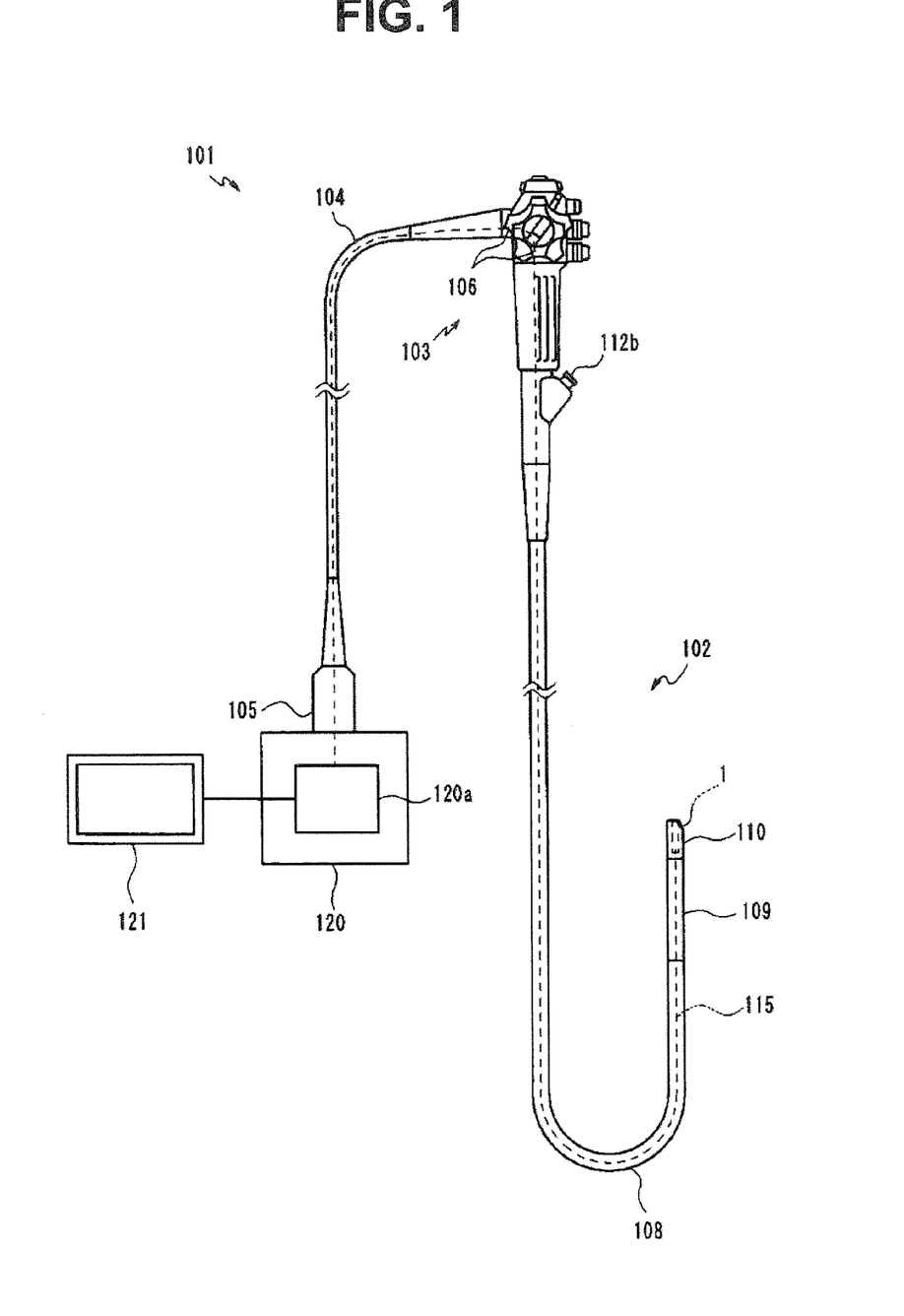
FIG. 1 is a diagram for explaining a configuration of an endoscope.

The endoscope 101 of the present embodiment is mainly configured by an elongated insertion section 102 introduced into an inside of the subject, an operation section 103 located at a proximal end of the insertion section 102, and a universal cord 104 extending from a side portion of the operation section 103.

The insertion section 102 is configured by concatenating a distal end portion 110 disposed at a distal end, a bendable bending section 109 disposed on a proximal end side of the distal end portion 110, and a flexible tube section 108 having flexibility disposed on a proximal end side of the bending section 109 and connected to a distal end side of the operation section 103. At the distal end portion 110, an image pickup unit 1 including an objective lens 10 and an image pickup device 2 and an opening portion 112a of a treatment instrument channel 112 are disposed. Note that the endoscope 101 may be an endoscope of a form called rigid endoscope not including a part having flexibility in an insertion section.

Figure 2:
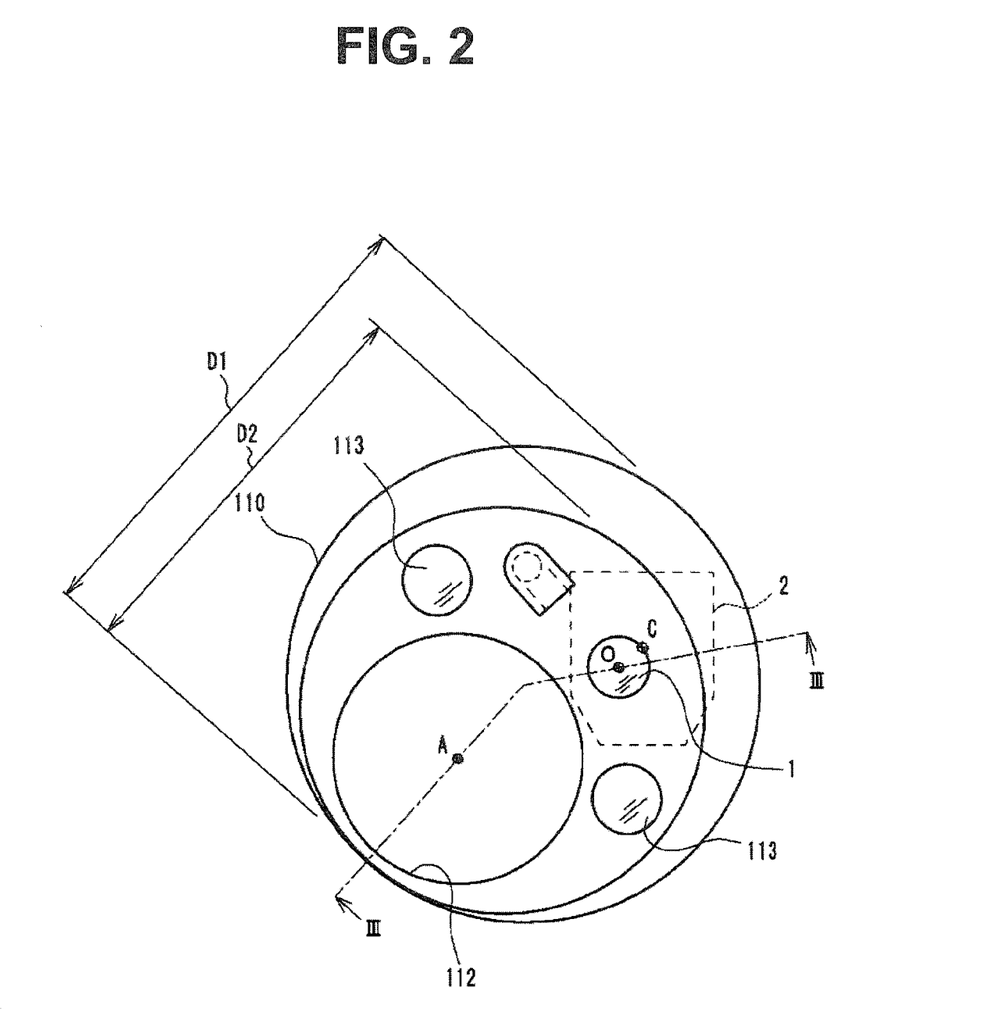
FIG. 2 is a front view of a distal end portion of the endoscope viewed from a front along an insertion axis.
Figure 3:
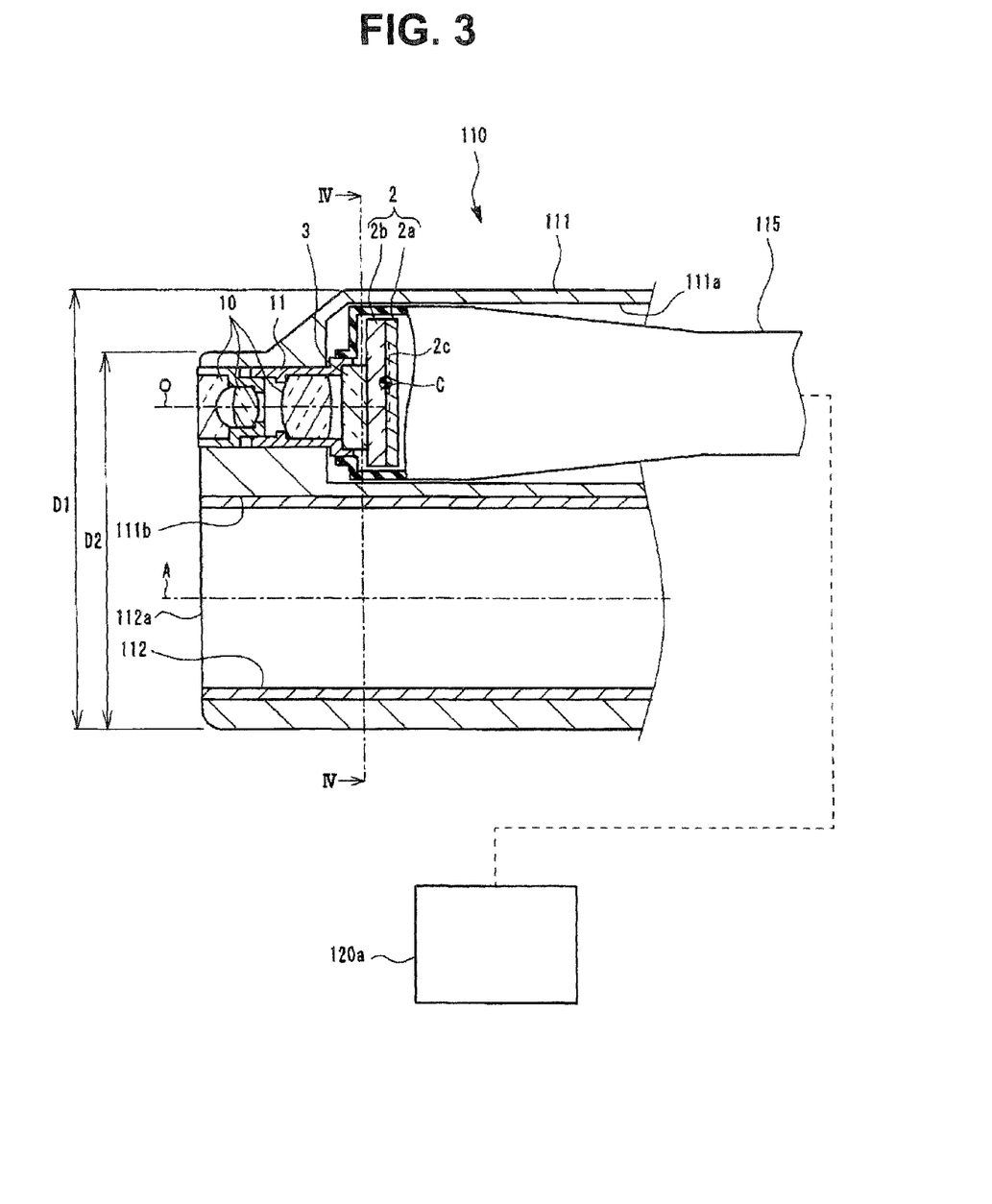
FIG. 3 is a sectional view of FIG. 2.
Figure 4:
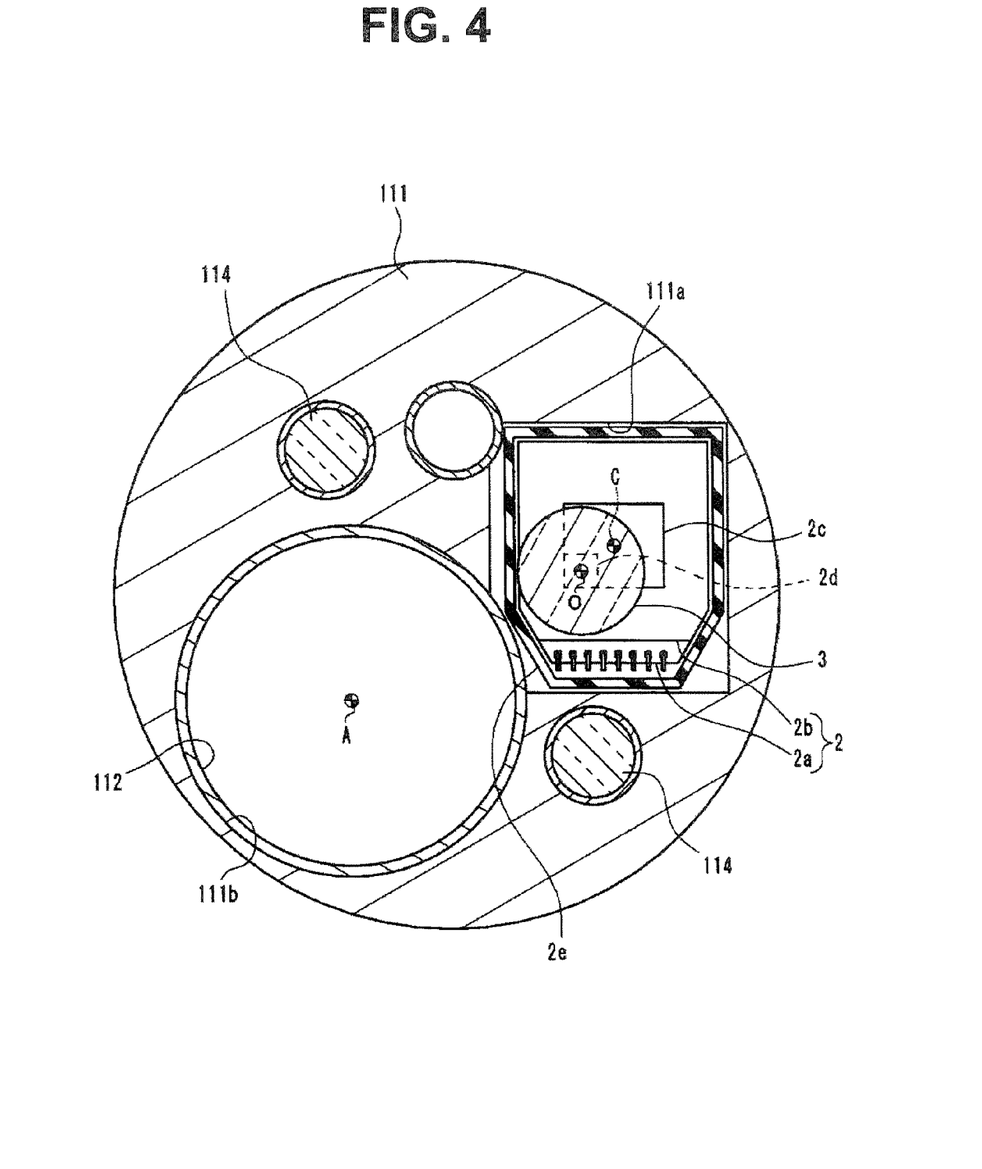
FIG. 4 is a IV-IV sectional view of FIG. 3.

FIG. 2 is a front view of the distal end portion 110 of the insertion section 102. FIG. 3 is a sectional view indicated by in FIG. 2. More specifically, a cross section of FIG. 3 includes a center axis A of the treatment instrument channel 112 and an optical axis O of the objective lens 10 of the image pickup unit 1. FIG. 4 is a IV-IV sectional view of FIG. 3.

As shown in FIG. 2 and FIG. 3, at the distal end portion 110, the image pickup unit 1, the opening portion 112a of the treatment instrument channel 112, and an illumination-light emitting section 113 (not shown in FIG. 3) are provided.

The image pickup unit 1 is fixed in a through-hole 111a formed in a distal-end rigid portion 111, which is a rigid member made of metal or synthetic resin, provided at the distal end portion 110. The through-hole 111a is formed along an insertion axis, which is a longitudinal direction of the distal end portion 110. The image pickup unit 1 is disposed to direct a visual field to a distal end direction of the distal end portion 110. A transmission cable 115 such as a coaxial cable extends from a proximal end side of the image pickup unit 1.

The treatment instrument channel 112 is a conduit inserted through the insertion section 102. The treatment instrument channel 112 causes the opening portion 112a opened at the distal end portion 110 and an opening portion 112b opening in the operation section 103 to communicate with each other. For example, by inserting a treatment instrument from the opening portion 112b, it is possible to project the treatment instrument from the opening portion 112a of the distal end portion 110 through the treatment instrument channel 112.

A distal end portion of the treatment instrument channel 112 is fixed in a state in which the distal end portion is inserted through a through-hole 111b formed in the distal-end rigid portion 111. The through-hole 111b is drilled adjacent to the through-hole 111a and in parallel to the through-hole 111a. Therefore, the opening portion 112a on a distal end side of the treatment instrument channel 112 is opened toward a distal end direction of the distal end portion 110 in a part adjacent to the image pickup unit 1. The opening direction of the opening portion 112a on the distal end side of the treatment instrument channel 112 and a direction of the visual field of the image pickup unit 1 substantially coincide with each other. The treatment instrument projecting from the opening portion 112a is present within the visual field of the image pickup unit 1.

In the illumination-light emitting section 113, a distal end of an optical fiber bundle 114 (not shown in FIG. 2 and FIG. 3) inserted through the insertion section 102 is disposed. Distal ends of the illumination-light emitting section 113 and the optical fiber bundle 114 are fixed to the distal-end rigid portion 111. The optical fiber bundle 114 extends from the distal-end rigid portion 111 toward the proximal end side of the insertion section 102.

In the operation section 103 disposed at the proximal end of the insertion section 102, an angle operation knob 106 for operating bending of the bending section 109 is provided. An endoscope connector 105 configured to be connectable to an external apparatus 120 is provided in a proximal end portion of the universal cord 104. The external apparatus 120, to which the endoscope connector 105 is connected, includes a light source device, a camera control unit 120a, and an image display section 121.

The transmission cable 115 and the optical fiber bundle 114 before mentioned are inserted through the insertion section 102, the operation section 103, and the universal cord 104. Proximal ends of the transmission cable 115 and the optical fiber bundle 114 are disposed in the endoscope connector 105.

The transmission cable 115 is configured to electrically connect the image pickup unit 1 and the connector section 105. The connector section 105 is connected to the external apparatus 120, whereby the image pickup unit 1 is electrically connected to the camera control unit 120a of the external apparatus 120 via the transmission cable 115. Supply of electric power from the external apparatus 120 to the image pickup unit 1 and exchange of signals between the external apparatus 120 and the image pickup unit 1 are performed via the transmission cable 115.

The camera control unit 120a has a configuration for generating a video based on a signal outputted from the image pickup unit 1 and outputting the video to the image display section 121. That is, in the present embodiment, an optical image picked up by the image pickup unit 1 is displayed on the image display section 121 as a video. Note that a part or all of the camera control unit 120a and the image display section 121 may be configured integrally with the endoscope 101.

The optical fiber bundle 114 is configured to transmit light emitted from the light source device included in the external apparatus 120 to the illumination-light emitting section 113 of the distal end portion 110. The illumination-light emitting section 113 is configured to emit light made incident from the optical fiber bundle 114 and illuminate the visual field of the image pickup unit 1. Note that the light source device may be disposed in the operation section 103 or the distal end portion 110 of the endoscope 101.

Next, a detailed configuration of the image pickup unit 1 is explained. The image pickup unit 1 includes the objective lens 10 and the image pickup device 2.

The objective lens 10 includes optical elements such as a lens and a filter and is configured to form an object image. In the present embodiment, as an example, the objective lens 10 is configured by a plurality of lenses disposed on the linear optical axis O. In the following explanation, a direction toward an object side along the optical axis O is referred to as object side and a direction opposite to the direction is referred to as image side.

The objective lens 10 is fixed in a cylindrical lens holding section 11. The lens holding section 11 has an outer diameter that fits in the through-hole 111a of the distal-end rigid portion 111. The lens holding section 11 fits in the through-hole 111a, whereby positioning of the image pickup unit 1 with respect to the distal-end rigid portion 111 is performed. The optical axis O of the objective lens 10 is parallel to the center axis A of the treatment instrument channel 112 in the distal-end rigid portion 111. Note that, in order to enable focus adjustment, the lens holding section 11 may be configured by a plurality of members divided in an optical axis direction.

The image pickup device 2 is disposed on the image side of the objective lens 10. The image pickup device 2 of the present embodiment is an image sensor capable of reading out a pixel signal from any selected pixel among a plurality of pixels such as a MOS image sensor or a CMOS image sensor. Detailed explanation of an operation principle and the like of such an image pickup device 2 is omitted because the operation principle and the like are publicly known.

The image pickup device 2 includes a device main body 2a in which a plurality of pixels made of photodiodes are formed on a device surface, which is one principal plane, and lid glass 2b stuck on the device surface in order to seal the device surface. The image pickup device 2 is disposed such that the device surface faces the object side and is orthogonal to the optical axis O. That is, the plane parallel to the device surface of the image pickup device 2 crosses the center axis A of the treatment instrument channel 112.

Cover glass 3 is stuck on a surface on the object side of the lid glass 2b by an adhesive. The cover glass 3 is formed in a disk shape having the optical axis O as a center axis and has an outer diameter that fits in a proximal end portion of the lens holding section 11. The cover glass 3 fits in the proximal end portion of the lens holding section 11, whereby positioning of the objective lens 10 and the image pickup device 2 is performed.

Note that the cover glass 3 does not have to directly fit in the lens holding section 11. For example, the cover glass 3 may fit in a cylindrical member that fits in the lens holding section 11 and may be positioned at the proximal end portion of the lens holding section 11 via the member.

As shown in FIG. 3 and FIG. 4, on the device surface of the device main body 2a of the image pickup device 2, all the pixels are formed in a pixel formation region 2c in a predetermined array. The pixel formation region 2c is, for example, rectangular or square. That is, the image pickup device 2 can convert an optical image formed in the pixel formation region 2c into an electric signal. In FIG. 4, a sign C is added to a position of a center (a center of gravity) of the pixel formation region 2c.

In the present embodiment, the pixel formation region 2c is disposed such that a center C is located in a place farther from the treatment instrument channel 112 than the optical axis O. In other words, in the present embodiment, the optical axis O is located in a place closer to the treatment instrument channel 112 than the center C of the pixel formation region 2c. That is, when viewed from a direction along the optical axis O, the objective lens 10 and the cover glass 3 are disposed to be shifted closer to the treatment instrument channel 112 than the center C of the pixel formation region 2c.

The endoscope 101 of the present embodiment generates a video to be displayed on the image display section 121 using a part of pixels in a region smaller than the pixel formation region 2c rather than generating a video to be displayed on the image display section 121 using all the pixels in the pixel formation region 2c. The region of the pixels used for signal generation for generating a video is defined as a segmentation region 2d.

Note that, when the endoscope 101 converts an optical image formed in the segmentation region 2d into a video to be displayed on the image display section 121, a form may be used in which a driving mode of the image pickup device 2 is set such that the image pickup device 2 outputs only a signal from the pixels located in the segmentation region 2d or a form may be used in which, after signals from all the pixels of the image pickup device 2 are read out, pixels are selected and a video of a region equivalent to the segmentation region 2d is read out in the external apparatus 120 and segmented in image processing.

A shape and a size of the segmentation region 2d are not particularly limited as long as the segmentation region 2d includes the number of pixels necessary for generation of a video and fits in the pixel formation region 2c. In the present embodiment, as an example, the segmentation region 2d is square. The segmentation region 2d may be rectangular or may be circular. The shape of the segmentation region 2d and an external shape of the video to be displayed on the image display section 121 do not have to be similar shapes. The external shape of the video to be displayed on the image display section 121 may be, for example, an octagonal shape obtained by cutting off four corners of a square.

As shown in FIG. 4, the segmentation region 2d is disposed such that a center (a center of gravity) is located in a place closer to the treatment instrument channel 112 than the center C of the pixel formation region 2c. In other words, a center of the segmentation region 2d is disposed to be shifted from the center C of the pixel formation region 2c toward the treatment instrument channel 112. More specifically, the center of the segmentation region 2d is disposed to be shifted from the center C of the pixel formation region 2c toward the center axis A of the treatment instrument channel 112. In the present embodiment, as an example, the center of the segmentation region 2d is located on the optical axis O of the objective lens 10. Note that the center of the segmentation region 2d does not have to coincide with the optical axis O.

As explained above, the endoscope 101 of the present embodiment includes, at the distal end portion 110 of the insertion section 102, the image pickup unit 1 including the image pickup device 2, which is the image sensor capable of reading out a pixel signal from any selected pixel among a plurality of pixels such as a MOS image sensor or a CMOS image sensor, and the treatment instrument channel 112 adjacent to the image pickup unit 1. In the image pickup device 2, in the pixel formation region 2c including all the pixels, the center of the segmentation region 2d including the plurality of pixels for reading out a signal for generating a video is disposed in a position closer to the treatment instrument channel 112 than the center C of the pixel formation region 2c.

In the endoscope 101 having such a configuration, the optical axis O of the objective lens 10 is closer to the treatment instrument channel 112 than the center C of the pixel formation region 2c. Therefore, as shown in FIG. 3, the objective lens 10 disposed farther on the distal end side than the image pickup device 2 is located close to a radial direction inner side of the distal end portion 110. Therefore, an outer diameter D2 of the distal end portion 110 farther on the distal end side than the image pickup device 2 can be set smaller than an outer diameter D1 of a position where image pickup device 2 is disposed. Therefore, in the endoscope 101 including the image sensor capable of reading out a pixel signal from any selected pixel among a plurality of pixels such as a MOS image sensor or a CMOS image sensor in which peripheral circuit formed around a pixel formation region is relatively large, it is possible to improve insertability of an insertion section.

By bringing the optical axis O of the objective lens 10 close to the treatment instrument channel 112, the treatment instrument projecting from the opening portion 112a of the treatment instrument channel 112 can be kept within the visual field of the image pickup unit 1 up to a vicinity of the opening portion 112a. That is, even if a projection distance of the treatment instrument from the opening portion 112a is short, since the treatment instrument is kept within the visual field of the image pickup unit 1, it is easy to operate the treatment instrument.

Note that, in the image pickup device 2 of the present embodiment, as shown in FIG. 4, a corner-cut-off chamfered portion 2e is formed at a corner portion adjacent to the treatment instrument channel 112. By forming the chamfered portion 2e at the corner portion of the image pickup device 2 in this way, it is possible to place the segmentation region 2d of the image pickup device 2 closer to the radial direction inner side of the distal end portion 110.

Figure 5:
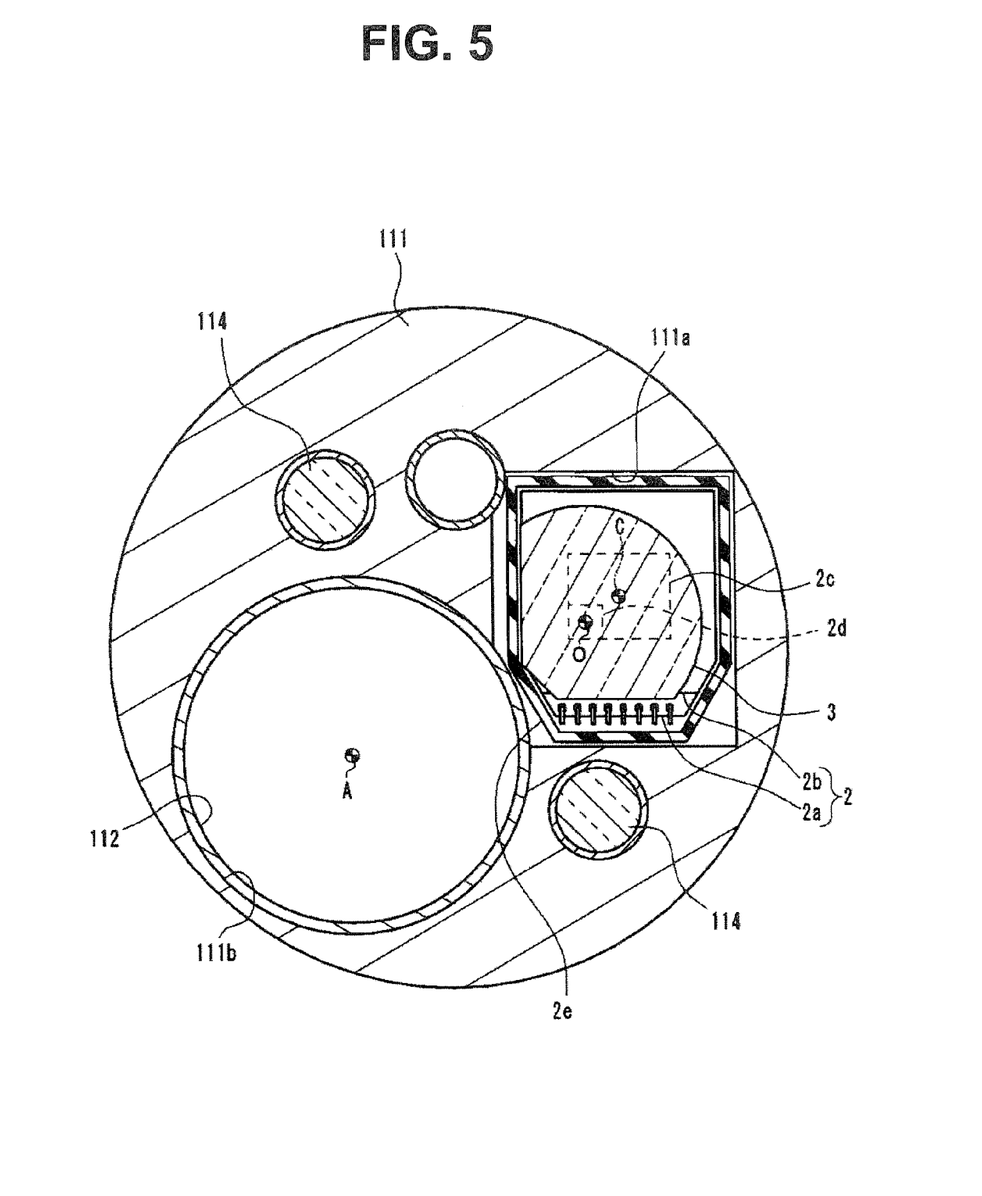
FIG. 5 is a diagram showing a first modification.

Note that, in the embodiment explained above, the cover glass 3 struck to the front surface of the image pickup device 2 is circular. However, the cover glass 3 does not have to be circular over an entire circumference. For example, as in a modification shown in FIG. 5, the cover glass 3 may have a circular shape partially cut off along an external shape of the image pickup unit 1.

Reflection of light on a side surface of the cover glass 3 causes a flare in a video. Therefore, the side surface of the cover glass 3 is desirably as far as possible from the segmentation region 2d. Therefore, as in the modification shown in FIG. 5, if an outer diameter of the circular cover glass 3 is increased and formed in a shape partially cut off to fit in the external shape of the image pickup unit 1, it is possible to suppress generation of the flare in the video.

Figure 6:
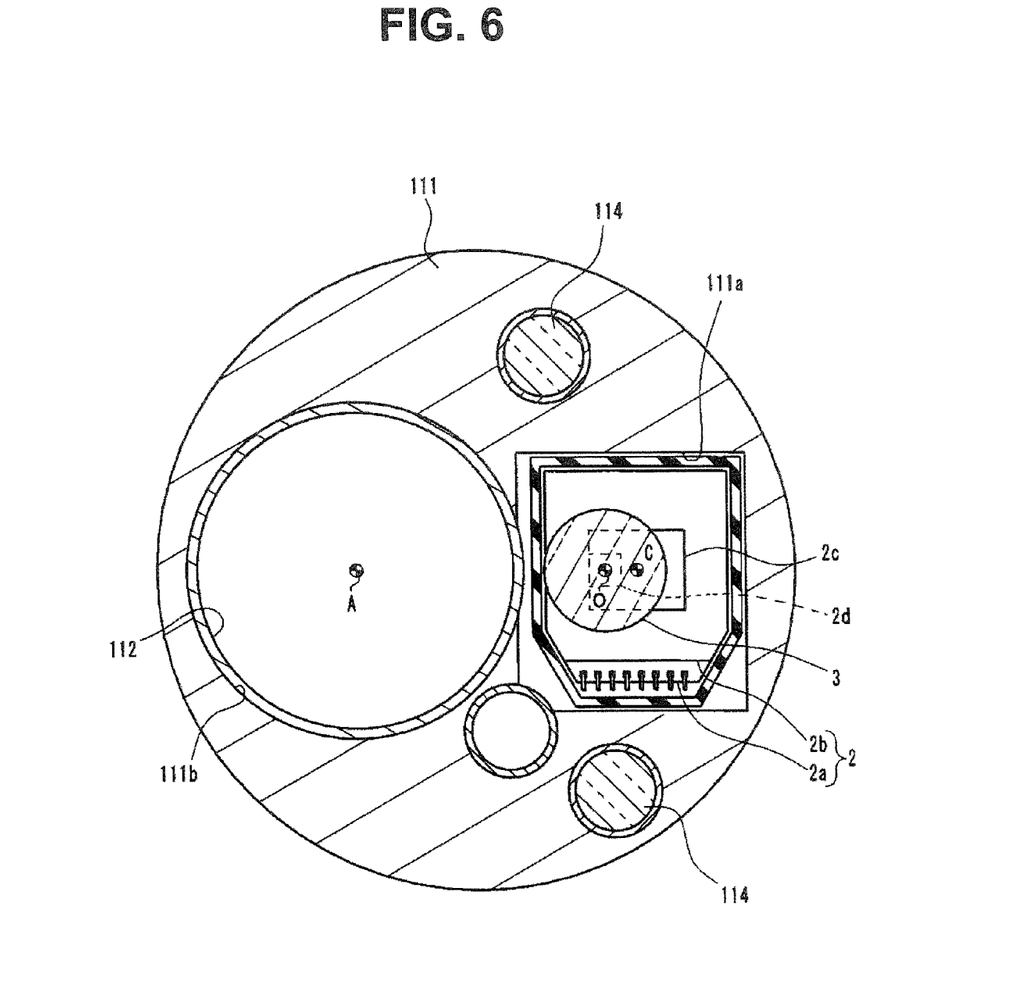
FIG. 6 is a diagram showing a second modification.

In the embodiment explained above, in the distal end portion 110, the image pickup unit 1 is disposed such that the corner portion where the chamfered portion 2e of the image pickup device 2 is formed is the closest to the treatment instrument channel 112. However, a relative positional relation between the image pickup unit 1 and the treatment instrument channel 112 is not limited to the present embodiment. For example, as shown in FIG. 6 as an example, a form may be adopted in which the image pickup unit 1 and the treatment instrument channel 112 are disposed such that a center portion of a short side of the rectangular pixel formation region 2c is the closest to the treatment instrument channel 112.

Second Embodiment

A second embodiment of the present invention is explained below. In the following explanation, only differences from the first embodiment are explained. Components same as the components in the first embodiment are denoted by the same reference numerals and signs and explanation of the components is omitted as appropriate.

Figure 7:
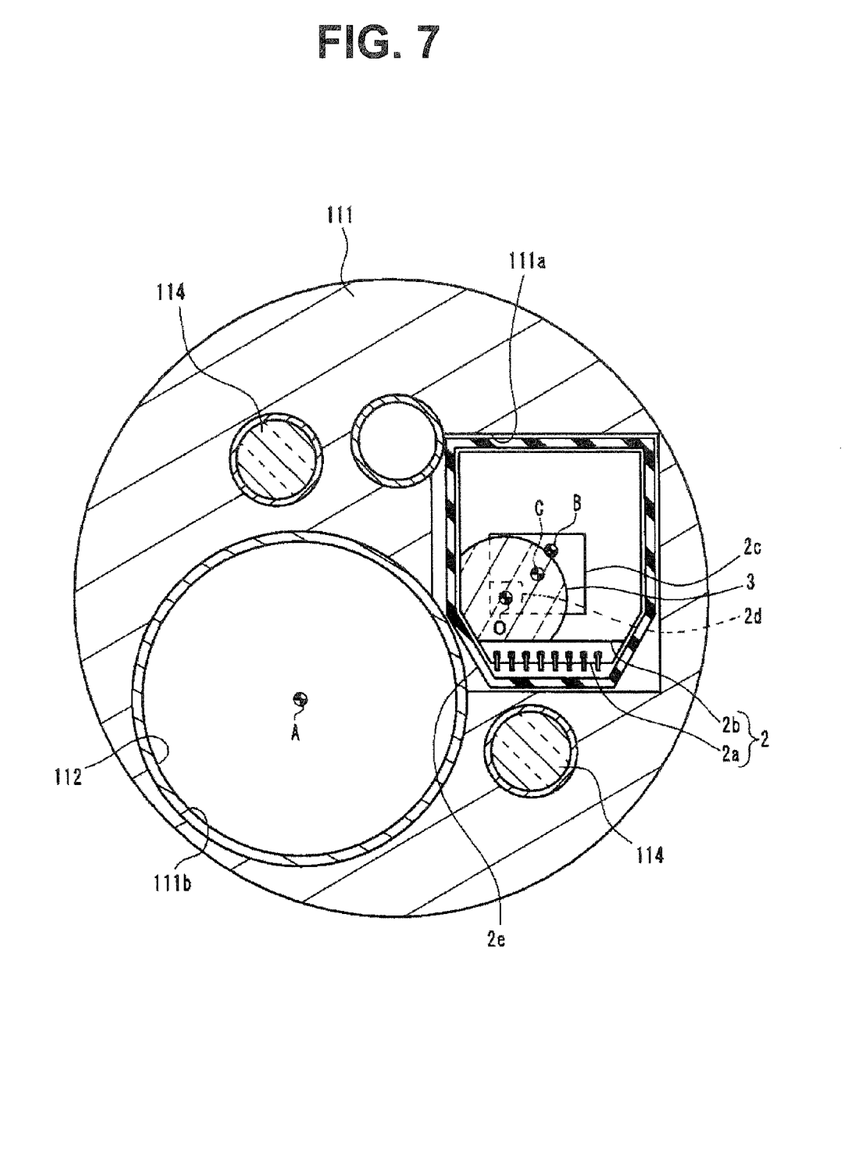
FIG. 7 is a diagram showing a second embodiment.

In the present embodiment, as shown in FIG. 7, the center C of the pixel formation region 2c of the image pickup device 2 is disposed in a position closer to the treatment instrument channel 112 than a center (a center of gravity) B of the external shape of the image pickup device 2 when viewed from a direction along the optical axis O. In other words, the center C of the pixel formation region 2c is disposed to be shifted from the center B of the external shape of the image pickup device 2 toward the treatment instrument channel 112. More specifically, the center C of the pixel formation region 2c is disposed to be shifted from the center B of the external shape of the image pickup device 2 toward the center axis A of the treatment instrument channel 112.

As in the first embodiment, the center of the segmentation region 2d is disposed in a position closer to the treatment instrument channel 112 than the center C of the pixel formation region 2c. In the present embodiment, as an example, the center of the segmentation region 2d is located on the optical axis O of the objective lens 10. Note that the center of the segmentation region 2d does not have to coincide with the optical axis O.

In this way, in the endoscope 101 of the present embodiment, on the device surface of the image pickup device 2, which is the image sensor capable of reading out a pixel signal from any selected pixel among a plurality of pixels such as a MOS image sensor or a CMOS image sensor, the pixel formation region 2c is provided in a position close to the treatment instrument channel 112. Consequently, in the present embodiment, compared with the first embodiment, it is possible to place the segmentation region 2d of the image pickup device 2 closer to the radial direction inner side of the distal end portion 110. It is possible to set the outer diameter D2 of the distal end portion 110 on the distal end side smaller than a diameter of the image pickup device 2.

Third Embodiment

A third embodiment of the present invention is explained below. In the following explanation, only differences from the first embodiment are explained. Components same as the components in the first embodiment are denoted by the same reference numerals and signs and explanation of the components is omitted as appropriate.

As explained above, in the image pickup device 2, the pixel formation region 2c is sealed by sticking the lid glass 2b on the device surface of the device main body 2a. There is a technique known for, in order to increase an amount of light reaching the pixels of the image pickup device 2, providing an air layer between the device main body 2a and the lid glass 2b by disposing an adhesive annularly around the pixel formation region 2c without filling the adhesive on the pixel formation region 2c. When the image pickup device 2 of the endoscope 101 is place under a highly humid environment, the air layer is required of high airtightness.

Figure 8:
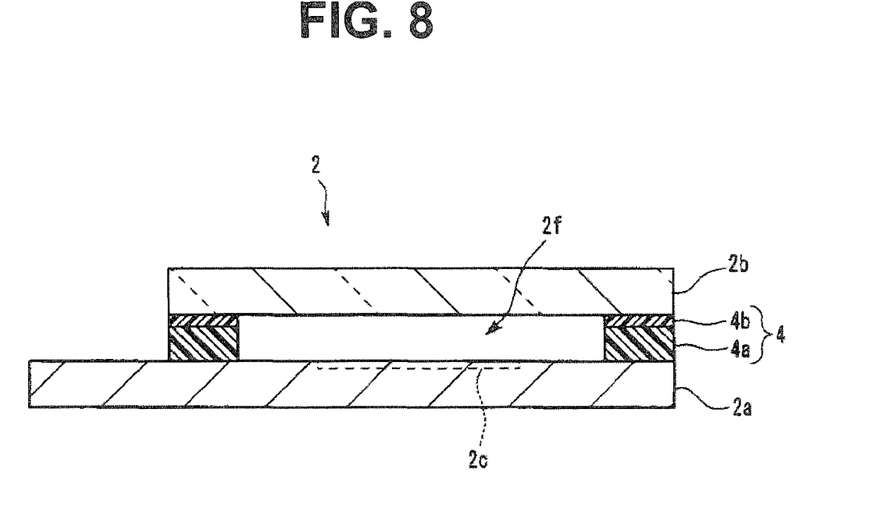
FIG. 8 is a diagram showing a third embodiment.

In the image pickup device 2 of the present embodiment, as shown in FIG. 8, the lid glass 2b is stuck on the device surface of the device main body 2a by a bonding section 4 having predetermined thickness disposed annularly (in a frame shape) around the pixel formation region 2c. Since the bonding section 4 is annular and has the predetermined thickness, an air layer 2f is formed between the pixel formation region 2c and the lid glass 2b.

The bonding section 4 is configured by a first adhesive 4a and a second adhesive 4b of two kinds having different viscosities before hardening. The first adhesive 4a and the second adhesive 4b are stacked in a thickness direction of the bonding section 4. The second adhesive 4b is disposed between the first adhesive 4a and the device main body 2a and/or the lid glass 2b. The first adhesive 4a has the viscosity before hardening higher than the viscosity before hardening of the second adhesive 4b. The first adhesive 4a is thicker than the second adhesive 4b and occupies most of thickness of the bonding section 4.

In the present embodiment explained above, the thickness of the bonding section 4 can be formed constant by the first adhesive 4a having the high viscosity without increasing the bonding section 4 in thickness. Adhesion of the bonding section 4 and the device main body 2a and/or the lid glass 2b can be increased by the adhesive 4b having the low viscosity. Therefore, in the image pickup device 2 of the present embodiment, it is possible to realize the air layer 2f having high airtightness.

Figure 9:
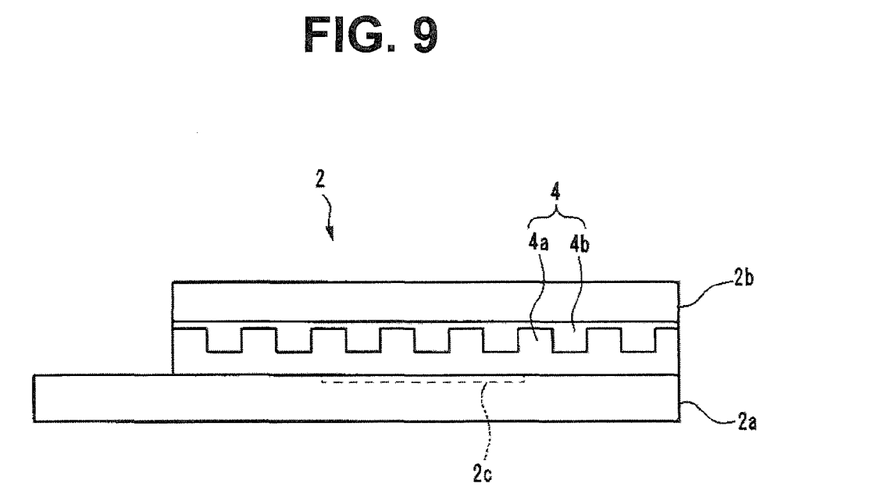
FIG. 9 is a diagram showing a first modification of the third embodiment.
Figure 10:
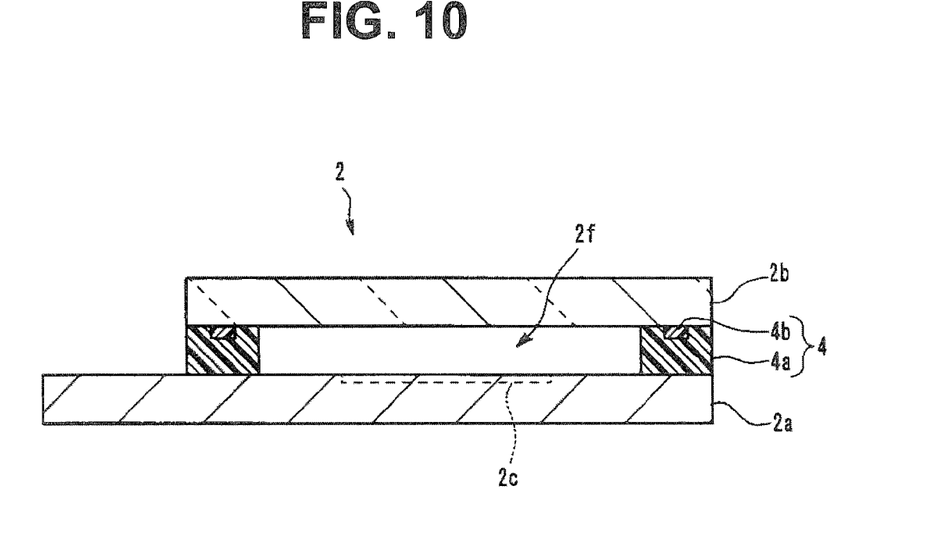
FIG. 10 is a diagram showing a second modification of the third embodiment.
Figure 11:
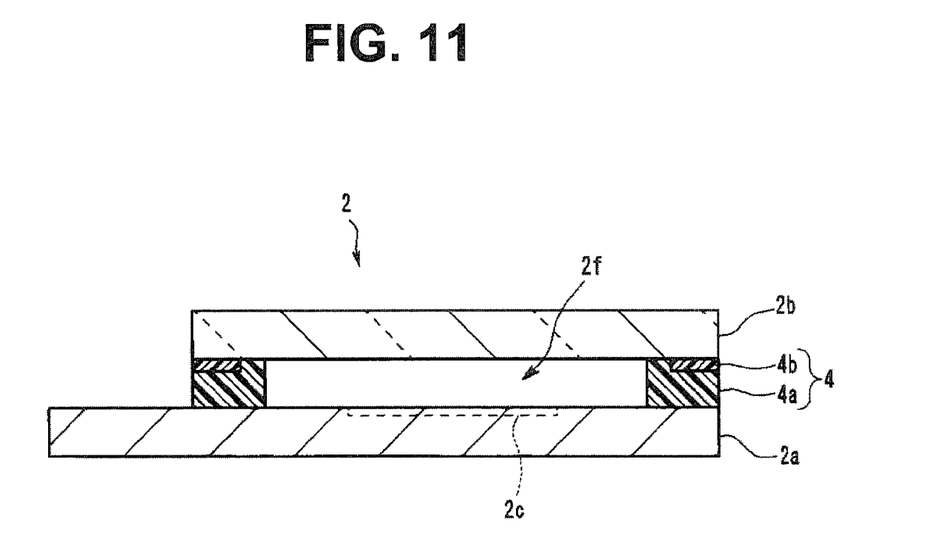
FIG. 11 is a diagram showing a third modification of the third embodiment.

Note that, in the bonding section 4, a ratio of the thickness of the first adhesive 4a and the second adhesive 4b does not have to be fixed in a circumferential direction. For example, as shown in FIG. 9, the ratio of the thicknesses of the first adhesive 4a and the second adhesive 4b may change in the circumferential direction of the annular bonding section 4. As shown in FIG. 10 and FIG. 11, the ratio of the thicknesses of the first adhesive 4a and the second adhesive 4b may change in a thickness direction (inward and outward directions) of the annular bonding section 4.

Figure 12:
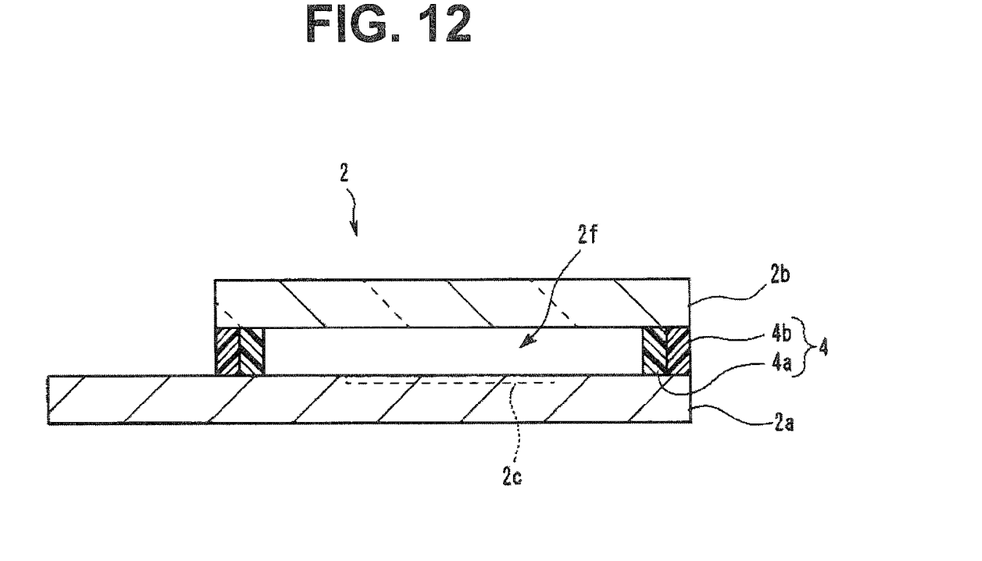
FIG. 12 is a diagram showing a fourth modification of the third embodiment.
Figure 13:
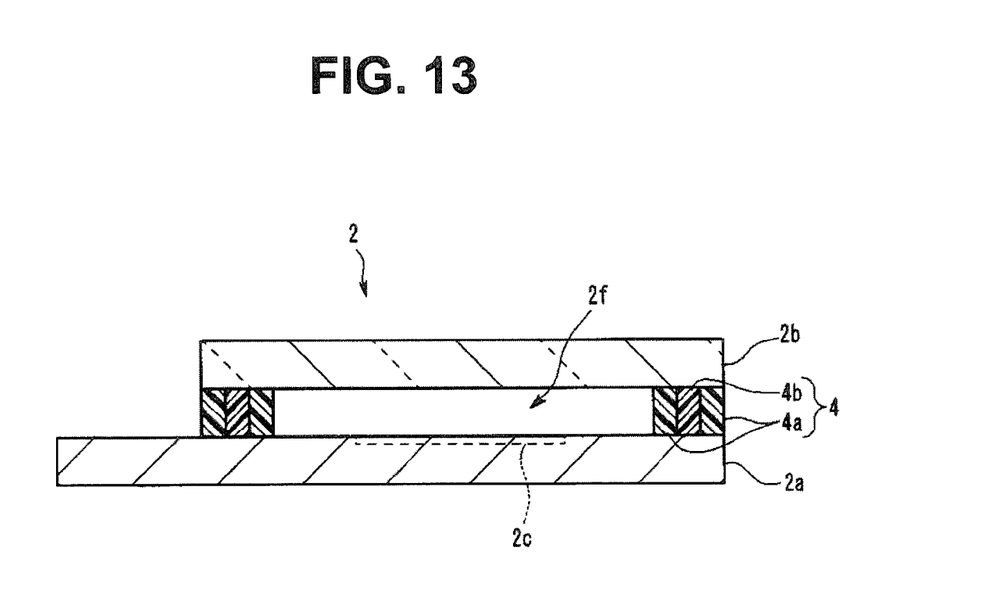
FIG. 13 is a diagram showing a fifth modification of the third embodiment.

As shown in FIG. 12 and FIG. 13, the bonding section 4 may be configured by the first adhesive 4a and the second adhesive 4b stacked in the thickness direction. In this case, the first adhesive 4a having the high viscosity is disposed at least on an innermost side. By disposing the first adhesive 4a having the high viscosity on the innermost side, it is possible to prevent the second adhesive 4b having the low viscosity from flowing onto the pixel formation region 2c in a stage before hardening.

The present invention is not limited to the embodiments explained above and can be changed as appropriate without departing from the gist or the idea of the invention read from the claims and the entire specification. An endoscope involving such a change is also included in the technical scope of the present invention.

What is claimed is:

1. An endoscope comprising:
a distal end portion provided at a distal end of an insertion section;
an image pickup unit provided at the distal end portion; and
a treatment instrument channel provided at the distal end portion, wherein
at the distal end portion, the image pickup unit and the treatment instrument channel are adjacent to each other,
the image pickup unit includes an objective lens, an image pickup sensor, a lens holding section, a first glass plate, and a second glass plate,
the image pickup sensor having a sensor surface on which pixels are formed, the image pickup sensor being disposed such that a plane parallel to the sensor surface crosses a center axis of the treatment instrument channel, the sensor surface having a pixel formation region comprising a plurality of pixels configured to receive an optical image from the objective lens and convert the optical image into an electric signal, the image pickup sensor being configured to be capable of reading out any pixel in the plurality of pixels, wherein the pixel formation region includes a segmentation region including less than all of the plurality of pixels of the pixel formation region to be read out for displaying a video, and a center of the segmentation region is shifted from a center of the pixel formation region toward the treatment instrument channel,
the first glass plate is disposed on the sensor surface of the image pickup sensor,
an optical axis of the objective lens is parallel to a center axis of the treatment instrument channel, and the center of the segmentation region is located on the optical axis,
the second glass plate is disposed on a distal surface of the first glass plate, a cross-sectional area of the second glass plate in the plane is smaller than a cross-section area of the first glass plate in the plane and the cross-sectional area of the second glass plate is larger than a cross-section area of the segmentation region in the plane, and
the lens holding section holds the objective lens, positions and holds the image pickup device with respect to the optical axis and holds the second glass plate proximally to the objective lens.

2. The endoscope according to claim 1, wherein the center of the segmentation region is disposed to be shifted from the center of the pixel formation region toward the center axis of the treatment instrument channel.

3. The endoscope according to claim 1, wherein the center of the pixel formation region is disposed to be shifted from a center of an external shape of the image pickup sensor toward the treatment instrument channel.

4. The endoscope according to claim 3, wherein the center of the pixel formation region is disposed to be shifted from the center of the external shape of the image pickup sensor toward the center axis of the treatment instrument channel.

5. The endoscope according to claim 1, wherein the image pickup sensor is a CMOS image sensor.

6. The endoscope according to claim 1, wherein the second glass plate is disposed such that a center of the second glass plate coincides with a center of the segmentation region.

7. The endoscope according to claim 1, wherein the image pickup sensor includes a corner-cut-off chamfered portion formed at a corner of the image pickup sensor, the corner-cut-off chamfered portion being positioned adjacent to the treatment instrument channel.

8. The endoscope according to claim 1, wherein the second glass plate is adhered to the distal surface of the first glass plate.

9. The endoscope according to claim 8, wherein the first glass plate is adhered to the sensor surface of the image pickup sensor.

* * * * *